United States Patent

Sanghvi et al.

[11] Patent Number: 5,873,902
[45] Date of Patent: Feb. 23, 1999

[54] ULTRASOUND INTENSITY DETERMINING METHOD AND APPARATUS

[75] Inventors: Narendra T. Sanghvi, Indianapolis, Ind.; Francis J. Fry, Port Charlotte, Fla.; Carl W. Hennige, San Jose; Claudio I. Zanelli, Sunnyvale, both of Calif.

[73] Assignee: Focus Surgery, Inc., Fremont, Calif.

[21] Appl. No.: 893,130

[22] Filed: Jul. 15, 1997

Related U.S. Application Data

[63] Continuation of Ser. No. 414,693, Mar. 31, 1995, abandoned.

[51] Int. Cl.[6] ............................................. A61F 7/00
[52] U.S. Cl. ............................................. 607/96; 600/438
[58] Field of Search ............................ 600/438, 440–441, 600/442, 443; 73/597, 599; 607/97–99; 601/3

[56] References Cited

U.S. PATENT DOCUMENTS

| | | | |
|---|---|---|---|
| 4,501,151 | 2/1985 | Christman | 600/437 X |
| 4,807,633 | 2/1989 | Fry | 600/438 |
| 5,361,767 | 11/1994 | Yukov | 128/660.06 |

FOREIGN PATENT DOCUMENTS

| | | | |
|---|---|---|---|
| 9319705 | 10/1993 | WIPO | 607/97 |

OTHER PUBLICATIONS

Hecht, Eugene, "Optics", Second Edition, Addison–Wesley, 1987.
Fry, William J. and Fry, Ruth Baumann, "Determination of Absolute Sound Levels and Acoustic Absorption Coefficients by Thermocouple Probes–Experiment", 26 J. Acous. Soc. Amer., 311–317, May, 1954.

*Primary Examiner*—Brian Casler
*Assistant Examiner*—Ryan Carter
*Attorney, Agent, or Firm*—Barnes & Thornburg

[57] ABSTRACT

A method of treatment by ultrasound comprises providing a first, ultrasound field intensity-to-voltage transducer sized for insertion into the vicinity of a treatment site and a second ultrasound treatment transducer. The free field intensities created by the second transducer in response to various second transducer exciting signal levels are determined. The first transducer outputs in the free field in response to various second transducer exciting signal levels are also determined. The first transducer is inserted into the vicinity of the treatment site, and the second transducer is positioned to create an ultrasound field at the treatment site. The distance from the second transducer to the first transducer is determined. An exciting signal is applied to the second transducer. The output of the first transducer is determined. The level of the exciting signal applied to the second transducer, the determined distance and the first transducer output are employed to determine the attenuation coefficient of the tissues between the second transducer and the first transducer.

11 Claims, 5 Drawing Sheets

ULTRASOUND INTENSITY DETERMINING METHOD AND APPARATUS

This application is a continuation, of application Ser. No. 08/414,693, filed Mar. 31, 1995, now abandoned.

BACKGROUND OF THE INVENTION

This invention relates to ultrasound treatment of body tissue. It is disclosed in the context of prostate ablation. However, it is believed to be useful in other contexts as well.

The ablation of tissue using ultrasound is known. In order to achieve ablation safely and optimally, knowledge of the power which must be supplied to the therapy transducer is essential. Generally there are guidelines for the required power, but these guidelines are not absolutely accurate, particularly where the tissue between the transducer and the treatment site is not homogeneous or where the treatment site is deep seated, that is, remote from the transducer. In the case of prostate ablation by focused ultrasound, for example, calcium or a fatty layer or both can lie between the colon, where the treatment transducer is ordinarily introduced into the body and resides in such treatment, and the treatment site in the prostate.

If the distance from the transducer to the treatment site is defined as L, then the intensity of the ultrasound field at the treatment site, $I_{site}$, can be defined as $$I_{site} = I_O \, \epsilon^{-\mu L}$$

where $I_0$ is the free field intensity of the ultrasound, e is the base of the natural logarithms, and $\mu$ is the so-called attenuation coefficient of the intervening tissue or other material. For ultrasound at a frequency of 4 MHz and water, $\mu \cong 0$. That is, ultrasound at this frequency passes essentially unattenuated through water. Thus, for any water path length, $I_{site} = I_O$. For other tissues typically encountered between the wall of the colon and the urethra where it passes through the prostate, $\mu$ has been determined empirically to lie somewhere in the range of 0.64/cm. However, in vitro studies of human tissues lying in this region have established that the attenuation coefficient can vary widely. Figures for $\mu$ as high as 1.0/cm and as low as 0.3/cm have been encountered. With this broad range of values it will be appreciated that a rather small variation in L can result in site intensities well below or well above those required to achieve prostate ablation, for example.

At ultrasound frequencies below about 15 MHz, the attenuation coefficient of warm-blooded animal tissues can be considered to be proportional to frequency. This is the so-called low frequency range generally considered the diagnostic (for example, visualization) and therapeutic range for ultrasound tissue ablation. It has been established that the attenuation coefficient in this range can be measured using thermocouples. There is, for example, Fry, William J. and Ruth Baumann Fry, "Determination of Absolute Sound Levels and Acoustic Absorption Coefficients by Thermocouple Probes-Experiment", 26 J. Acous. Soc. Amer., 311, May, 1954. These observations are combined in the present invention to provide apparatus and a method for determining the treatment transducer's output in the free field in order to provide sufficient ultrasound intensity at a site to achieve a desired therapeutic effect.

SUMMARY OF THE INVENTION

According to an aspect of the invention, a method of treatment by ultrasound comprises providing a first, ultrasound field intensity measuring transducer sized for insertion into the vicinity of a treatment site and a second ultrasound generating treatment transducer. The free field intensities created by the generating transducer in response to various generating transducer exciting signal levels are determined. The measuring transducer outputs in the free field in response to various generating transducer exciting signal levels are also determined. The measuring transducer is inserted into the vicinity of the treatment site, and the generating transducer is positioned to create an ultrasound field at the treatment site. The distance from the generating transducer to the measuring transducer is determined. An exciting signal is applied to the generating transducer. The output of the measuring transducer is determined. The level of the exciting signal applied to the generating transducer, the determined distance and the measuring transducer output are employed to determine the attenuation coefficient of the tissues between the generating transducer and the first transducer.

According to an illustrative embodiment of this aspect of the invention, the method further comprises moving the generating transducer to at least one additional position, and repeating the above steps for the at least one additional position of the generating transducer. The step of determining from the level of the exciting signal applied to the generating transducer, the determined distance and the measuring transducer output the attenuation coefficient comprise determining at least one additional attenuation coefficient. Illustratively according to this aspect of the invention, the method further comprises the steps of storing the attenuation coefficient and the at least one additional attenuation coefficient. The attenuation coefficient is recalled when the generating transducer is positioned to create an ultrasound field at the treatment site. The exciting signal level required to produce the desired ultrasound field intensity at the treatment site is then determined, and the required exciting signal level is generated. The desired ultrasound field intensity at the at least one additional treatment site is determined. The at least one additional attenuation coefficient is recalled when the generating transducer is in the at least one additional position. At least one additional exciting signal level required to produce the desired ultrasound field intensity at the at least one additional treatment site is determined, and the at least one additional exciting signal level is generated.

Illustratively according to this aspect of the invention, the method comprises establishing a desired ultrasound field intensity at a location closer to the generating transducer than the measuring transducer, and establishing the distance from the generating transducer to that closer location. The desired ultrasound field intensity at that closer location, the determined attenuation coefficient and the distance from the generating transducer to that closer location are used to determine the generating transducer exciting signal level required to produce the desired ultrasound field intensity at that closer location.

Additionally illustratively according to this aspect of the invention, a desired ultrasound field intensity at a location more remote from the generating transducer than the measuring transducer is established. The distance from the generating transducer to that more remote location is established. The desired ultrasound field intensity at that more remote location, the determined attenuation coefficient and the distance from the generating transducer to that more remote location are used to determine the generating transducer exciting signal level required to produce the desired ultrasound field intensity at that more remote location.

Illustratively according to this aspect of the invention, the method further comprises the steps of determining the desired ultrasound field intensity at the treatment site, introducing the generating transducer adjacent the treatment site, determining the distance from the generating transducer to the treatment site, and determining the exciting signal level required to produce the desired ultrasound field intensity at the treatment site.

Illustratively according to this aspect of the invention, the measuring transducer comprises either a thermocouple or a hydrophone.

According to another aspect of this invention, a thermocouple comprises first and second thermocouple leads, and a thermocouple junction. A rigid support provides a first lumen for the first and second leads. The first lumen has a first end beyond which the junction extends and a second end through which access is provided to the leads. A resin bead is formed over the junction and supported by the rigid support at the first end.

Illustratively according to this aspect of the invention, a flexible tube has a second lumen through which access is provided to the leads. The flexible tube has first and second ends. One of the second end of the rigid support and first end of the flexible tube is press fitted into the other of the second end of the rigid support and first end of the flexible tube.

Additionally illustratively the resin bead comprises a generally spherical resin bead and the junction is positioned substantially at the center of the resin bead.

Illustratively the resin bead comprises a urethane bead. The rigid support comprises a length of stainless steel tubing. The flexible tube comprises a length of PTFE tubing.

BRIEF DESCRIPTION OF THE DRAWINGS

The invention may best be understood by referring to the following detailed description and accompanying drawings which illustrate the invention. In the drawings.

DETAILED DESCRIPTION OF ILLUSTRATIVE EMBODIMENTS

Figure 1:
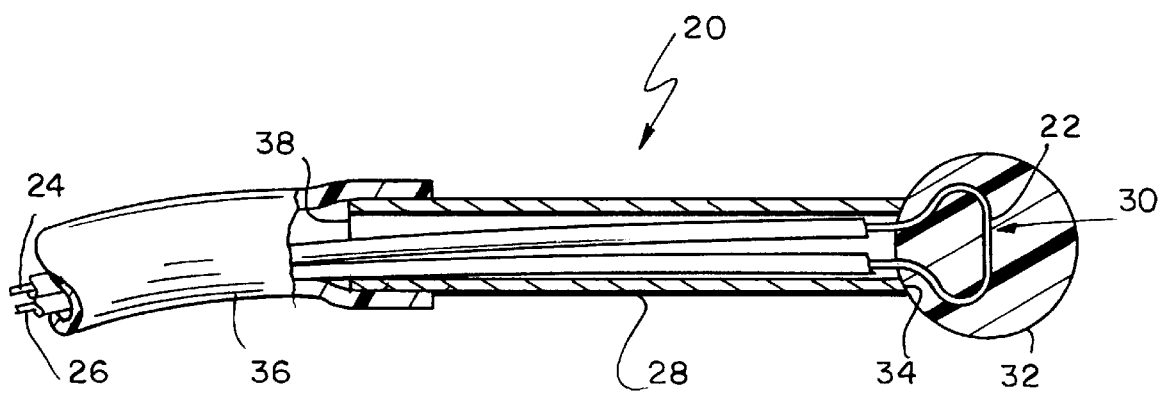
FIG. 1 illustrates an enlarged, fragmentary, partial longitudinal sectional view of an apparatus constructed according to an aspect of the present invention.

Referring now to FIG. 1, the apparatus 20 of the present invention includes a copper-constantan butt joint thermocouple 22 formed from about 1–2 mil (about 0.025–0.05 mm) diameter wire. The insulated thermocouple leads 24, 26 are threaded through a tubular stainless steel standoff 28 about 3 mm in length and with about a 0.36 mm outside diameter. The thermocouple junction 30 is imbedded at the center of an optically transparent urethane sphere 32 having a diameter of about 1 mm formed at one end 34 of the standoff 28. The insulated leads 24, 26 are then threaded through an extremely flexible Teflon PTFE tube 36 and the other end 38 of the standoff 28 is press fitted into the Teflon tube 36. Where ultrasound prostate 37 ablation is to be conducted by ultrasound induced hyperthermia, the apparatus 20 is positioned in the urethra 39 by insertion through a standard urethral catheter 40 which is then retracted to expose the apparatus 20.

This apparatus 20 construction renders the thermocouple 22 substantially non-directional and phase-insensitive. When the apparatus 20 is placed at any desired position in the free field in water, it can be calibrated against any primary standard ultrasound source to yield absolute ultrasound intensity at any tissue site. This is so, provided the apparatus 20 is placed in the same sound field configuration as used in the free field. This condition is readily achieved by using the same exciting ultrasound source for free field calibration and tissue ultrasound excitation. Additionally, under short burst excitation, typically 0.1 sec. or less, the thermocouple 22 output is primarily a function of ultrasound intensity and thermocouple bead 32 material, and is unaffected by surrounding tissue, for example.

Turning now to FIGS. 2a–e, a method according to the invention will be explained. In the method of determining ultrasound field intensity $I_{site}$ at a treatment site 42, for a typical, relatively sharply focused ultrasound therapy transducer 44, the beam 46 intensity profiles 47, 49, both across 48 (FIG. 2b) the beam 46 (the so-called transverse or radial beam intensity profile 47) and along 50 (FIG. 2c) the beam 46 (the so-called longitudinal beam intensity profile 49), are developed at as many points in the ultrasound field 46 as are desired using a hydrophone in a water bath. All of these intensities are then stored, illustratively, electronically, for later use. The technician will ordinarily want the treatment site 42 to coincide with the focus of the treatment transducer 44. In this way, the temperatures of all remaining tissue in the beam 46 will be controlled.

Figure 2A:
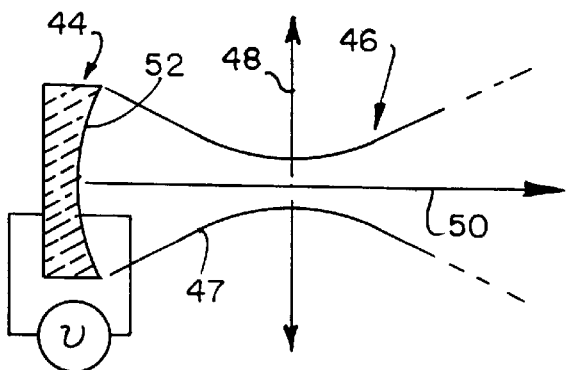
FIG. 2a illustrates a highly diagrammatic partly longitudinal sectional view of an apparatus useful in methods according to an aspect of the present invention.
Figure 2B:
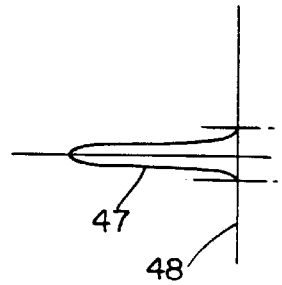
FIGS. 2b–e illustrate graphically relationships useful in understanding the present invention.
Figure 2C:
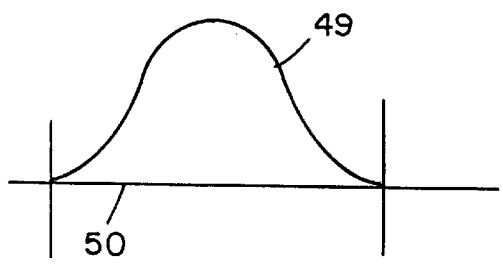
Figure 2D:
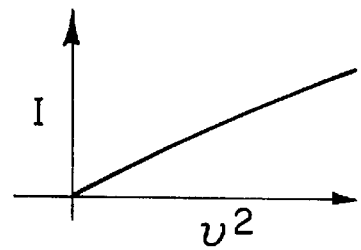
Figure 2E:
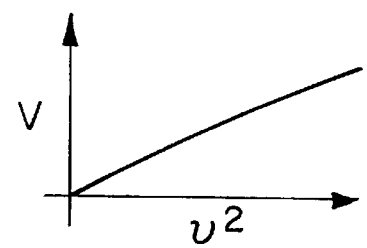

Recall that in the water bath the attenuation coefficient $\mu$ is effectively zero. This intensity at any point in the beam 46 is the result of the interaction of the intensities at all points on the active surface 52 of the transducer 44. Thus for any ultrasound transducer 44 and any location along 50 or across 48 the beam 46, an intensity I versus input power or $v^2$ relationship (FIG. 2d) can be developed, where $v^1$ is the square of the input voltage v to the ultrasound transducer 44. Next, the hydrophone is replaced in the water bath by the apparatus 20, and the transducer 44 is energized with short pulses, 0.1 sec. or so, of ultrasound at the same voltages. Because the pulses are short, the technician can be assured that any thermocouple 22 output voltage V related in time to the pulse timing is a result of the input voltage, v, to the transducer 44. A relationship can then be plotted between $v^2$ and the thermocouple 22 output voltage V at as many points in the ultrasound field 46 as are desired (FIG. 2e). It should also be noted that V is directly proportional to thermocouple 22 temperature. This exercise thus permits a further relationship between ultrasound field intensity and temperature to be developed where that is necessary or desirable.

Figure 3:
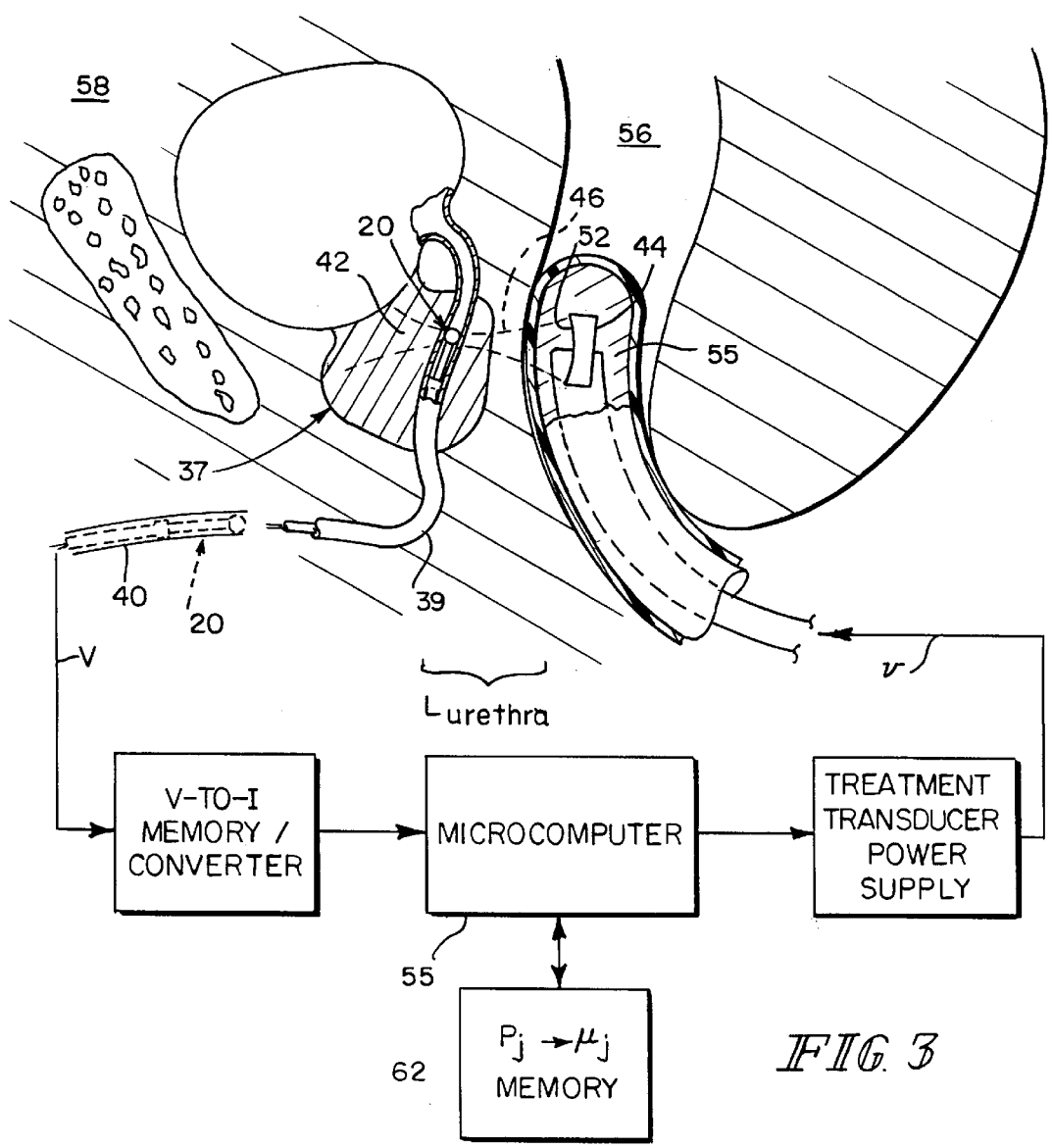
FIG. 3 illustrates an anterior to posterior sectional view of certain details of male human anatomy, with certain apparatus according to an aspect of the present invention illustrated diagrammatically.

After the V versus $v^2$ relationship (FIG. 2e) is developed, the apparatus 20 is placed in the urethral catheter 40 and inserted into the urethra 39 to a depth in the prostate 37 (See FIG. 3). The transducer 44 is ultrasonically coupled 55 to the wall of the colon 56 and imaging is performed either using the treatment transducer 44 in an imaging mode or an associated imaging transducer. In either event, a distance $L_{urethra,j}$ along a treatment path $P_j$ between the treatment transducer 44 and the thermocouple 22, which is readily visible during imaging, is ascertained. Thus, all of the variables in the equation $I_{site}=I_O \varepsilon^{-\mu 1}$ except $\mu$ are known: $I_O$ from the water bath measurement of intensity I versus applied transducer voltage squared, $v^2$; $I_{site}$ from the output voltage V of the thermocouple and the relationships between V and applied transducer voltage squared, $v^2$, and intensity I and applied transducer voltage squared, $v^2$; and $L=L_{urethra\ j}$ from the imaging exercise. A microcomputer 55 controller for the transducer 44 can be programmed to obtain $\mu_j$ for a particular treatment pathway $P_j$, and use $\mu_j$, and the value of $I_O$ obtained from the square of the voltage applied to the transducer to treat by ablation prostate 37 tissue lying at distances L either less than, that is, toward the colon 56 from, or greater than, that is, beyond the urethra 39 toward the front of the abdomen 58 from, the distance $L_{urethra\ j}$ to the thermocouple 22 along the selected treatment pathway $P_j$. It should be understood that this technique assumes that $\mu_j$ of any treatment pathway $P_j$ does not change beyond the urethra 39.

Figure 4:
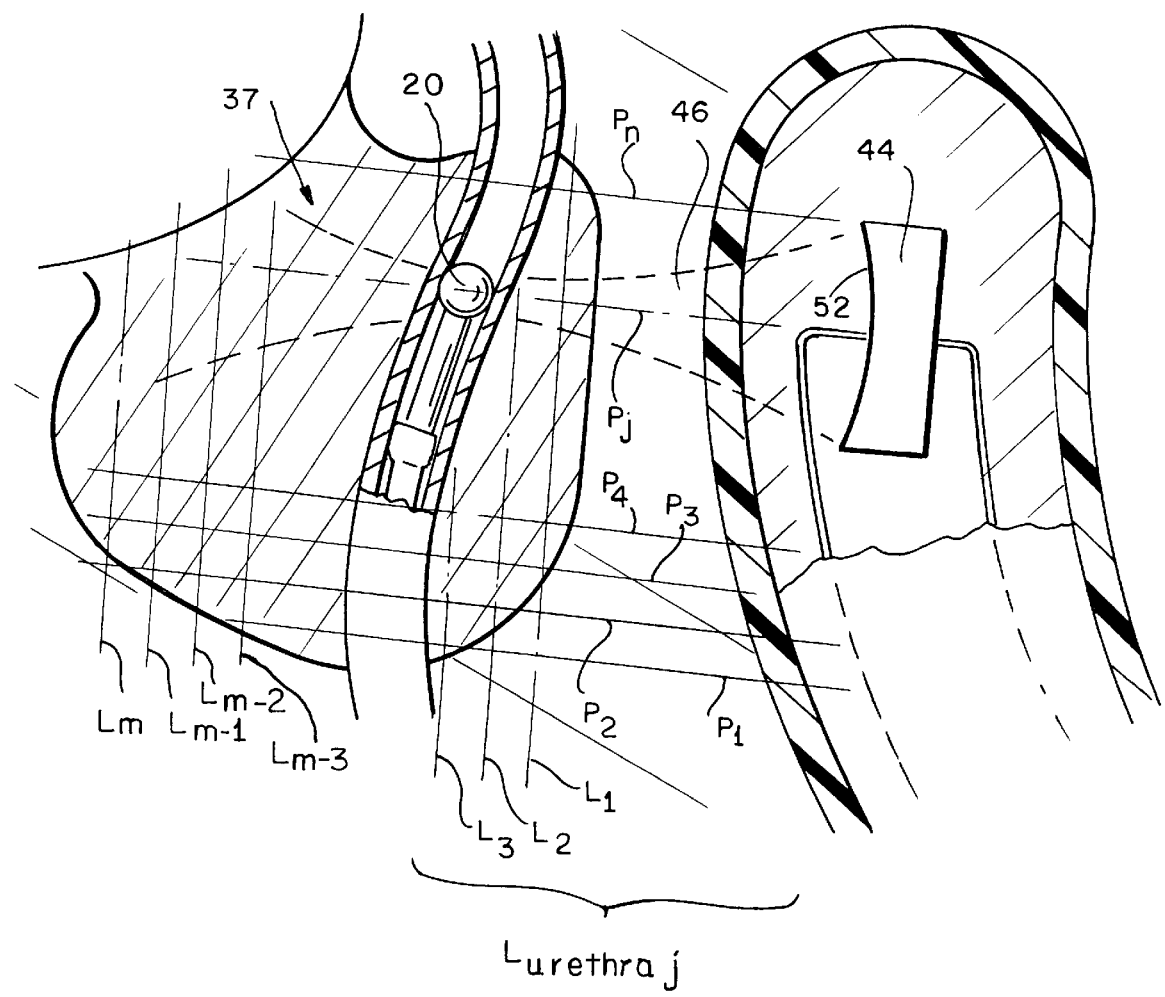
FIG. 4 illustrates an enlarged view of certain details of FIG. 3 with an overlying grid of treatment pathways $P_1$, $P_2$, ... $P_j$, ... $P_n$ and treatment depths $L_1$, $L_2$, ... $L_m$ useful in understanding the present invention.

Referring to FIG. 4, this technique yields extremely precise control of prostate 37 ablation treatment along multiple pathways $P_1, P_2, \ldots P_n$ within a particular patient's prostate 37. The different $\mu$'s, $\mu_1, \mu_2, \ldots \mu_n$ of the n different treatment pathways $P_1, P_2, \ldots P_n$, each having m treatment depths $L_1, L_2, \ldots L_m$ within the prostate 37, can be stored in the microcomputer 55's memory 62 and recalled during the treatment under the control of the microcomputer 55 effectively to automate the prostate 37 ablation process. The pathways $P_1, P_2, \ldots P_n$ extend generally along the axis of the transducer 44 and through its focus at its various locations in the colon 56. Movement of the apparatus 20 and/or treatment transducer 44 to place it/them on any selected treatment path $P_j$ can also be automated under microcomputer 55 control or can be manual. If a treatment transducer 44 having a fixed focal length is employed, different focal length treatment transducers may desirably be employed to treat the prostate 37 at different depths $L_1$, $L_2, \ldots L_m$. If a variable focus transducer is employed, the focal length of the variable focus transducer can also be controlled by microcomputer 55.

Figure 5:
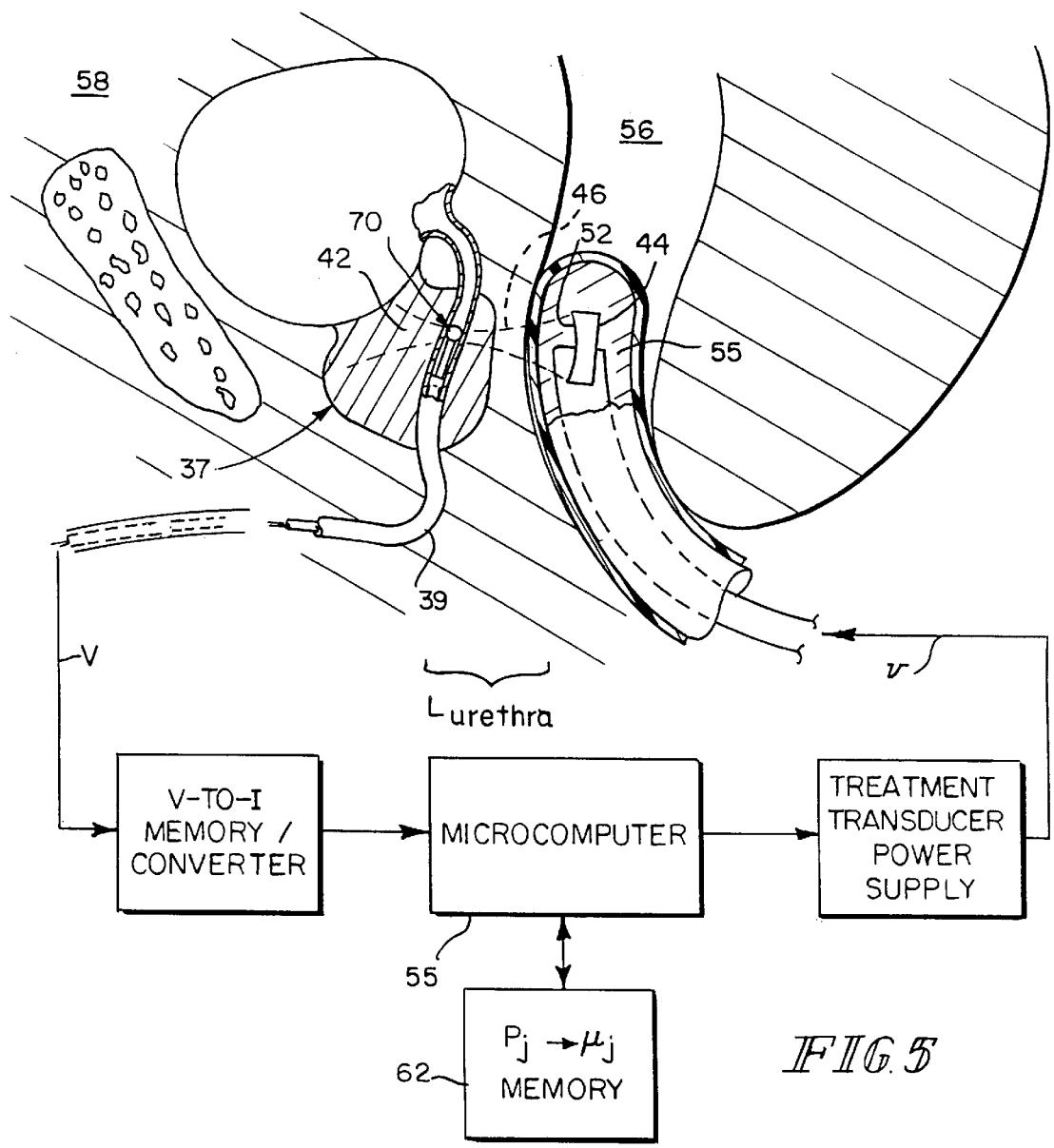
FIG. 5 illustrates an anterior to posterior sectional view of certain details of male human anatomy, with certain apparatus according to an aspect of the present invention illustrated diagrammatically.

In another embodiment of the method illustrated in FIG. 5, the hydrophone 70 is not replaced after calibration in the free field, the water bath, with the apparatus 20. Rather, the active area of the hydrophone 70 itself is inserted into the treatment site, using the same techniques as are available to insert the apparatus 20. The hydrophone 70 is perfectly acceptable for this purpose. Considerable care should be taken, however, that the hydrophone assume the same orientation with respect to the ultrasound field in the treatment site as it assumed with respect to the ultrasound field in the free field. This is so because such hydrophones are known to be directional. In both of the illustrated embodiments, the ultrasound transducer 44 was driven by a Panametrics 5052 P/R pulser/receiver. In the embodiment of FIG. 5, the hydrophone 70 employed was a Medi-Tech Sonicate 6 French catheter with hydrophone S/N 1833.

What is claimed is:

1. A method of determining the ultrasound attenuation coefficient of tissue comprising the steps of providing an ultrasound field intensity measuring transducer sized for insertion into the vicinity of a treatment site, providing an ultrasound field generating transducer, determining the free field intensity created by the generating transducer in response to various generating transducer exciting signal levels, determining the measuring transducer output in the free field in response to various generating transducer exciting signal levels, inserting the measuring transducer into the vicinity of the treatment site, positioning the generating transducer to create an ultrasound field at the treatment site, determining the distance from the generating transducer to the measuring transducer, applying an exciting signal to the generating transducer, determining the measuring transducer output, and determining the attenuation coefficient of the tissues between the generating transducer and the measuring transducer.

2. The method of claim 1 and further comprising moving the generating transducer to at least one additional position, and repeating the steps of claim 1 for the at least one additional position of the generating transducer, the step of determining the attenuation coefficient comprising determining at least one additional attenuation coefficient.

3. The method of claim 2 and further comprising the steps of storing the attenuation coefficient and the at least one additional attenuation coefficient, recalling the attenuation coefficient when the generating transducer is positioned to create an ultrasound field at the treatment site, determining the exciting signal level required to produce the desired ultrasound field intensity at the treatment site, generating the required exciting signal level, determining the desired ultrasound field intensity at the at least one additional treatment site, recalling the at least one additional attenuation coefficient when the generating transducer is in the at least one additional position, determining at least one additional exciting signal level required to produce the desired ultrasound field intensity at the at least one additional treatment site, and generating the at least one additional exciting signal level.

4. The method of claim 1 comprising establishing a desired ultrasound field intensity at a location closer to the generating transducer than the measuring transducer, establishing the distance from the generating transducer to that closer location, and determining the generating transducer exciting signal level required to produce the desired ultrasound field intensity at that closer location.

5. The method of claim 1 comprising establishing a desired ultrasound field intensity at a location more remote from the generating transducer than the measuring transducer, establishing the distance from the generating transducer to that more remote location, and determining the generating transducer exciting signal level required to produce the desired ultrasound field intensity at that more remote location.

6. The method of claim 1 and further comprising the steps of determining the desired ultrasound field intensity at the treatment site, introducing the generating transducer adjacent the treatment site, determining the distance from the generating transducer to the treatment site, and determining the exciting signal level required to produce the desired ultrasound field intensity at the treatment site.

7. The method of claim 1, 2, 3, 4, 5 or 6 wherein the step of providing a measuring transducer comprises the step of providing a thermocouple.

8. The method of claim 1, 2, 3, 4, 5 or 6 wherein the step of providing a measuring transducer comprises the step of providing a hydrophone.

9. The method of claim 1 wherein the step of inserting the measuring transducer into the vicinity of the treatment site comprises inserting the measuring transducer into the vicinity of the treatment site using a catheter.

10. The method of claim 1 wherein the step of inserting the measuring transducer into the vicinity of the treatment site comprises inserting the measuring transducer into a canal in the vicinity of the treatment site.

11. The method of claim 1 wherein the step of positioning the generating transducer to create an ultrasound field at the treatment site comprises positioning the generating transducer adjacent an internal body surface.

* * * * *